(12) United States Patent
Schwint et al.

(10) Patent No.: US 7,910,784 B2
(45) Date of Patent: Mar. 22, 2011

(54) PROCESS FOR THE PRODUCTION OF STYRENE MONOMER BY IMPROVING ENERGY EFFICIENCY AND INJECTING A RECYCLE GAS INTO THE EB VAPORIZER

(75) Inventors: Kevin J. Schwint, Long Valley, NJ (US); Richard J. Wilcox, West Caldwell, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 310 days.

(21) Appl. No.: 12/139,456

(22) Filed: Jun. 14, 2008

(65) Prior Publication Data

US 2009/0312590 A1  Dec. 17, 2009

(51) Int. Cl.
*C07C 5/327* (2006.01)
(52) U.S. Cl. .................. 585/444; 585/443; 585/440
(58) Field of Classification Search ............ 585/444, 585/443, 440
See application file for complete search history.

(56) References Cited

U.S. PATENT DOCUMENTS

| | | | |
|---|---|---|---|
| 3,904,484 A | 9/1975 | King | |
| 4,628,136 A | 12/1986 | Sardina | |
| 4,765,398 A | 8/1988 | Tsao | |
| 5,053,572 A | 10/1991 | Kim et al. | |
| 6,958,427 B2 * | 10/2005 | Park et al. | 585/444 |
| 7,034,195 B2 | 4/2006 | Schindler et al. | |
| 2007/0225532 A1 | 9/2007 | Tonkovich et al. | |

FOREIGN PATENT DOCUMENTS

KR  10-2006-0092305  8/2006

OTHER PUBLICATIONS

International Search Report, Jul. 21, 2009.

* cited by examiner

*Primary Examiner* — Thuan Dinh Dang
(74) *Attorney, Agent, or Firm* — Osha • Liang LLP

(57) ABSTRACT

This invention relates to a process for the production of styrene monomer by the dehydrogenation or oxidative dehydrogenation of ethylbenzene in the presence of recycle gas and more particularly to a method of reducing the boiling point of liquid ethylbenzene feed in the production of styrene monomer. The process comprises the step of catalytically dehydrogenating or oxydehydrogenating ethylbenzene in the presence of a mixture, wherein the mixture substantially comprises carbon dioxide, thereby catalytically producing styrene monomer.

10 Claims, 1 Drawing Sheet

US 7,910,784 B2

PROCESS FOR THE PRODUCTION OF STYRENE MONOMER BY IMPROVING ENERGY EFFICIENCY AND INJECTING A RECYCLE GAS INTO THE EB VAPORIZER

FIELD OF THE INVENTION

This invention relates to a process for the production of styrene monomer by the dehydrogenation of ethylbenzene in the presence of recycle gas and more particularly to a method of reducing the boiling point of liquid ethylbenzene feed in the production of styrene monomer.

BACKGROUND

Styrene is a basic building block for the manufacture of a broad range of materials. It is used to make polystyrene, acrylonitrile-butadiene-styrene, polyester resins, synthetic rubber, and a host of other products.

Production of styrene by dehydrogenation of ethylbenzene is commonly conducted by mixing ethylbenzene with steam and passing the mixture through a dehydrogenation catalyst-packed bed. Steam is used as the diluent gas in the dehydrogenation reaction system to supply heat needed for the endothermic reaction of ethylbenzene to styrene. Steam/water is also used to lower the boiling point of the ethylbenzene feed, either at the azeotropic composition (i.e. minimum boiling point) or at some non-azeotropic composition (i.e. reduced boiling point). See U.S. Pat. Nos. 4,628,136 and 4,765,398, each incorporated herein in the entirety. The vaporized ethylbenzene/steam is mixed with the diluent steam/water before feeding the dehydrogenation reactors, so the water contained therein is complementary to the dilution stream required in the reaction system.

Lowering the boiling point of ethylbenzene allows the use of low level heat to vaporize the ethylbenzene feed to the dehydrogenation reaction system. Despite the use of steam/water to lower the boiling point of ethylbenzene feed, the use of steam reduces the overall energy efficiency of the process. As an alternative, Samsung Total Petrochemicals Co. (Korean Patent Pub. No. 20060092305) used inert gas in place of all or part of the steam to reduce the boiling point of the ethylbenzene feed. However, the addition of inerts to the reactor feed adds to the raw material requirements of the process and the offgas compressor load and power requirements. The inert gas may also not be entirely inert, and may detrimentally affect the equilibrium reaction of ethylbenzene dehydrogenation or the catalyst activity.

A process that economically lowers the boiling point of the ethylbenzene feed in an oxidative ethylbenzene dehydrogenation process has not been reported. As such, there exists an ongoing and unmet need in the industry for economical and energy efficient methods for styrene monomer production from ethylbenzene feedstocks.

SUMMARY OF THE INVENTION

This invention relates to a process for the production of styrene monomer (i.e. styrene) by the dehydrogenation or oxidative dehydrogenation (oxydehydrogenation) of ethylbenzene in the presence of recycle gas. The invention achieves a lowering of the boiling point of ethylbenzene feed by injecting recycle gas in place of all or some of the steam/water typically used in conventional styrene monomer processes. In one aspect, the recycle gas mainly comprises carbon dioxide.

In one embodiment, the invention is directed to a process for the production of styrene monomer from ethylbenzene comprising the steps of feeding liquid ethylbenzene feedstock into a vaporizer unit (i.e. vaporizer) capable of converting liquid ethylbenzene to gaseous ethylbenzene, wherein the vaporizer unit produces an overhead comprising gaseous ethylbenzene; feeding a mixture into said vaporizer unit, wherein the mixture comprises an amount of recycle carbon dioxide sufficient to lower the boiling point of ethylbenzene at least 5° C.; heating the vaporizer thereby converting liquid ethylbenzene to gaseous ethylbenzene, wherein the gaseous ethylbenzene is recovered in the vaporizer overheads; and catalytically dehydrogenating or oxydehydrogenating the ethylbenzene in the vaporized overheads thereby catalytically producing a styrene monomer.

The invention is also directed to a process for the production of styrene monomer from ethylbenzene comprising the steps of feeding liquid ethylbenzene feedstock into a vaporizer unit capable of converting liquid ethylbenzene to gaseous ethylbenzene, wherein the vaporizer unit produces an overhead comprising gaseous ethylbenzene; feeding a mixture into said vaporizer unit, wherein the mixture comprises approximately 2-5 moles of recycle carbon dioxide for each mole of ethylbenzene; heating the vaporizer thereby converting liquid ethylbenzene to gaseous ethylbenzene, wherein the gaseous ethylbenzene is recovered in the vaporizer overheads; and catalytically oxydehydrogenating the ethylbenzene in the vaporized overheads thereby catalytically producing a styrene monomer.

Advantages of using recycle gas comprising carbon dioxide to reduce the boiling point of ethylbenzene feed are (1) carbon dioxide is the diluent, and thus inherent, in the oxydehydrogenation (ODH) reaction system as carbon dioxide is normally fed relative to ethylbenzene at approximately 5:1 (molar ratio) in the ODH process; (2) ample amount of carbon dioxide is available in the system to dilute the ethylbenzene in the vaporizer meaning that additional (e.g. fresh) carbon dioxide feed is not required; (3) carbon dioxide sparged into the ethylbenzene vaporizer complements the carbon dioxide required for reaction system dilution and does not add to the carbon dioxide recycle gas requirements; (4) carbon dioxide is the main component in the recycle gas feeding the reaction system on the ODH process; (5) carbon dioxide has a very low normal boiling point; and (6) carbon dioxide is not inert and may be used as a "soft" oxidant in the reaction system. These advantages are given by way of non-limiting example only, and additional benefits and advantages will be readily apparent to those skilled in the art in view of the description set forth herein.

DETAILED DESCRIPTION OF THE INVENTION

Figure 1:
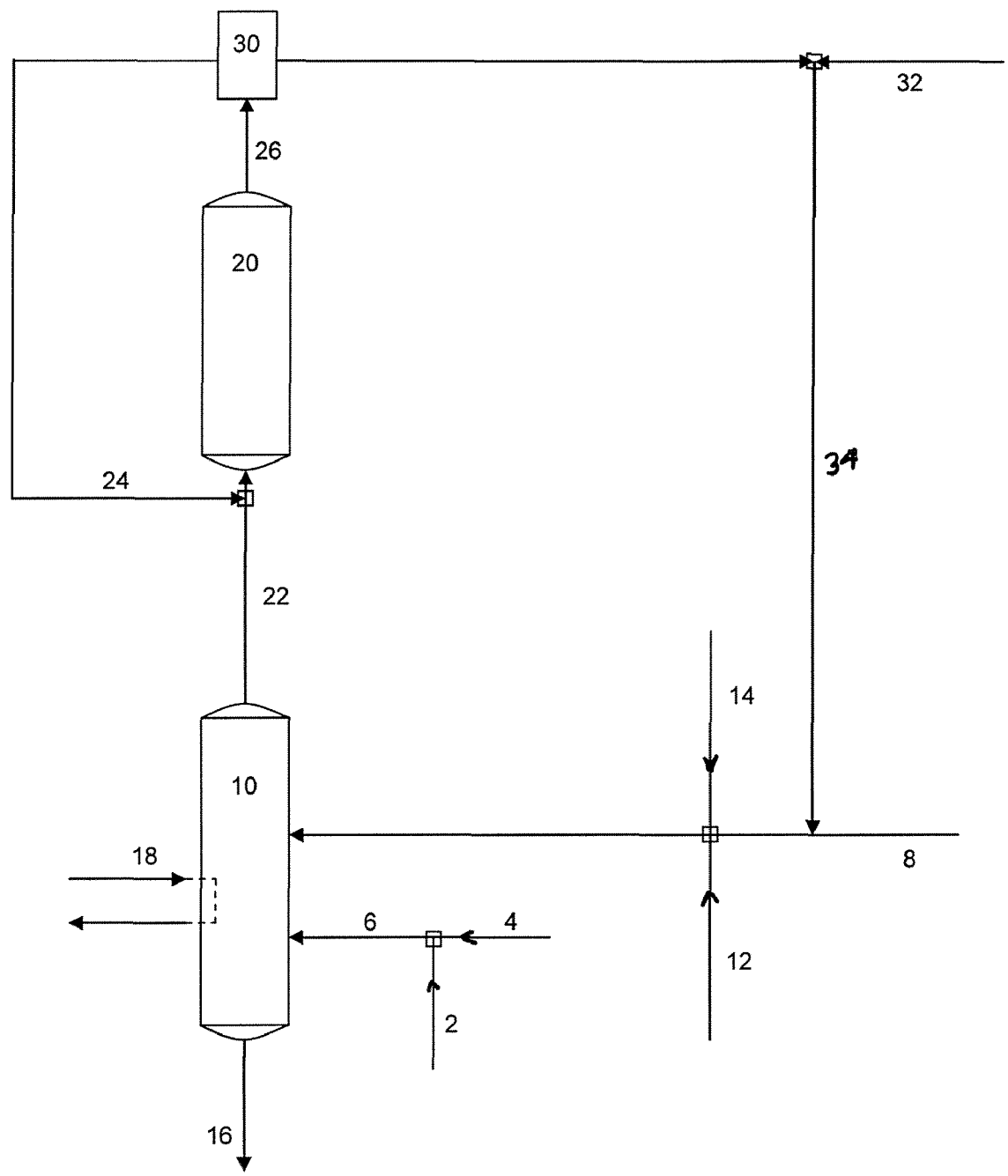
FIG. 1 is a flowchart showing one embodiment of the present invention wherein liquid ethylbenzene is converted to gaseous ethylbenzene and catalytically dehydrogenated to styrene monomer. Ethylbenzene feedstocks are mixed with recycle gas comprising carbon dioxide, and optionally steams and or inert gases in a vaporizer. The vaporizer is capable of converting liquid ethylbenzene to gaseous ethylbenzene using less heat energy than conventionally systems.

This invention relates to a process for the production of styrene monomer by the dehydrogenation of ethylbenzene in the presence of recycle gas, mainly carbon dioxide. More particularly, the invention relates to a method of reducing the boiling point of liquid ethylbenzene feed in the production of styrene monomer.

Carbon dioxide may be supplied to the ethylbenzene vaporizer from recycle gas, fresh feed or combinations thereof. Preferably, the carbon dioxide source is a recycle gas. In a preferred embodiment, the recycle gas comprises approximately 50 volume % to 100 volume % carbon dioxide, more preferably approximately 90 volume % carbon dioxide. Impurities may be present in the recycle gas. Some examples of impurities may include carbon monoxide, hydrogen, methane, argon, nitrogen and trace amounts of aromatic and aliphatic hydrocarbons.

The recycle carbon dioxide based oxidative dehydrogenation process of the present invention differs from the prior art in the following aspects. Recycle gas comprising carbon dioxide is sparged into the ethylbenzene vaporizer instead of, or supplemented with, steam/water. Preferably recycle gas/water mixtures, recycle gas/inert gas mixtures and recycle gas/inert gas/water mixtures may be sparged into the ethylbenzene vaporizer. Carbon dioxide is preferred because it has better thermophysical properties (e.g. lower boiling point) than water for the purpose of lowering the boiling point of ethylbenzene mixtures. And, a fresh feed of carbon dioxide is not required. Recycle carbon dioxide from the oxyhydrogenation process may be used, which does not increase the offgas compressor load and power requirements.

In one embodiment, the present invention is directed to a process for the production of styrene monomer from ethylbenzene comprising the steps of feeding liquid ethylbenzene feedstock into a vaporizer unit capable of converting liquid ethylbenzene to gaseous ethylbenzene, wherein the vaporizer unit produces an overhead comprising gaseous ethylbenzene; feeding a mixture into said vaporizer unit, wherein the mixture comprises recycle carbon dioxide sufficient to lower the boiling point of ethylbenzene at least 5° C.; heating the vaporizer thereby converting liquid ethylbenzene to gaseous ethylbenzene, wherein the gaseous ethylbenzene is recovered in the vaporizer overheads; and catalytically dehydrogenating or oxydehydrogenating the ethylbenzene in the vaporized overheads thereby catalytically producing a styrene monomer.

As used herein, the term "ethylbenzene feedstocks" refers to hydrocarbon mixtures containing ethylbenzene. Preferably, the feedstock contains pure ethylbenzene, recycled ethylbenzene or combinations thereof.

As used herein, the term "vaporizer unit" refers to an ethylbenzene vaporizer used to convert liquid ethylbenzene to gaseous ethylbenzene. Preferably, gaseous ethylbenzene is recovered in the overheads and a liquid blowdown comprising heavy impurities contained in the ethylbenzene feed, together with some ethylbenzene, is recovered in the bottoms.

As used herein, the term "catalytic dehydrogenation" refers to a process for the continuous heterogeneously catalyzed partial dehydrogenation of a hydrocarbon in the gas phase.

As used herein, the term "catalytic oxidative dehydrogenation" or "catalytic oxydehydrogenation" refers to a process for the continuous heterogeneously catalyzed partial dehydrogenation of a hydrocarbon in the gas phase and in the presence of carbon dioxide and/or molecular oxygen.

FIG. 1 shows one embodiment of the present invention wherein styrene monomer is produced by the catalytic dehydrogenation of ethylbenzene. Ethylbenzene feedstock (6) is fed into a vaporizer (10). The ethylbenzene feedstock may comprise pure ethylbenzene (2), recycled ethylbenzene (4) or mixtures thereof. Recycle gas (8) is also fed into the vaporizer (10). Recycle gas may be combined with steam (12), inert gas (14) or both. The vaporizer (10) is heated with a heat source (18) to convert liquid ethylbenzene to gaseous ethylbenzene. Residual heavies and liquid ethylbenzene is recovered from the vaporizer bottoms (16) and ethylbenzene contained therein may be recycled into the ethylbenzene feedstock (4) after recovery by fractionation. The vaporized ethylbenzene/recycle gas may be recovered from the overheads of the vaporizer (22) and fed into a dehydrogenation system (20). Optionally, the vaporized ethylbenzene/recycle gas may be combined with additional recycle gas (24) and fed into the dehydrogenation unit (20).

The dehydrogenation unit (20) may be any type of dehydrogenation or oxydehydrogenation unit used to produce styrene monomer from EB, in particular units using $CO_2$ as an oxidant. The ethylebenzene vaporizer flow typically used in prior dehydrogenation or oxydehydrogenation unit is replaced with that of the present invention. The ethylbenzene vaporizer may be used, for example, in the oxydehydrogenation system described in U.S. patent application Ser. No. 12/139,455 titled "Styrene Monomer Process Based on Oxidative Dehydrogenation of Ethylebenzene Using $CO_2$ as a Soft Oxidant" and filed on Jun. 14, 2008, the entire contents of which are hereby incorporated by reference. The effluent from the dehydrogenation unit (26) may be processed to separate styrene product from the recycle gas (40). The styrene product is sent through line (32) for further processing. In some embodiments, a portion of the recycle gas may be fed back to the dehydrogenation unit (20) through line (24). In other embodiments, part or all of the recycle gas may be fed through line (34) back to the EB vaporizer (10).

In one embodiment, the recycle gas (8) may be supplied from the styrene monomer process or from a separate process (32). For example, the recycle gas (8) may be a small slip stream from the overheads of a flux oil scrubber which is diverted from a Recycle Gas Heater to the vaporizer unit and sparged into the liquid ethylbenzene. The resulting ethylbenzene/recycle gas mixture has a boiling point significantly below that of pure ethylbenzene.

In a further embodiment, the heat source (18) may be condensed low pressure steam (condensing temperature approximately 100° C.-110° C.) or low temperature process streams (e.g. ethylbenzene/styrene monomer Splitter overheads with a condensing temperature approximately 97° C.-103° C., ethylbenzene Recovery Column overheads with a condensing temperature approximately 108° C.-123° C., etc.). These heat sources are at a lower temperature and more economical than using medium pressure or high pressure steam to vaporize the ethylbenzene feed. The heat recovery from process streams (process interchange) reduces the overall utility consumption (i.e. steam and cooling water), resulting in significant economic savings.

Preferably, the addition of sufficient recycle gas to the ethylbenzene vaporizer lowers the boiling point of ethylbenzene below approximately 122° C. at approximately 760 mm Hg. Most preferably, the addition of sufficient recycle gas to the ethylbenzene vaporizer lowers the boiling point of ethylbenzene below approximately 105° C. at approximately 760 mm Hg. As one skilled in the art recognizes, temperature and pressure vary inversely. As the pressure of the system changes from 760 mm Hg, the comparable temperature value will also change. Comparable temperature/pressure values equivalent to 89° C.-110° C./760 mm Hg may be used and are contemplated by the present invention.

Preferably, the range of recycle carbon dioxide for each mole of ethylbenzene is approximately 0.5-5 moles. More preferably, the range of recycle carbon dioxide for each mole of ethylbenzene is approximately 1-2 moles. Most preferably, the range of recycle carbon dioxide for each mole of ethylbenzene is approximately 1.5 moles.

In another embodiment, the additional recycle gas (24) may comprise approximately 2.0 moles carbon dioxide per mole of ethylbenzene and may be recovered downstream, for example, from a Second Stage Oxidizer or equivalent. The combined additional recycle gas (24) and vaporized ethylbenzene/recycle gas (22) are preferably combined into an oxidative dehydrogenation at the required carbon dioxide/ethylbenzene molar ratio of approximately 3.5.

In another embodiment, because of the split of recycle gas between a Recycle Gas Heater and the ethylbenzene vaporizer, it may be preferable to split the reactor effluent between the Recycle Gas Heater and an additional ethylbenzene Feed Heater for better heat recovery. The reactor effluent may be split between the two heaters in proportion to the split of recycle gas between the ethylbenzene feed vaporizer and the Recycle Gas Heater.

The oxidative dehydrogenation of ethylbenzene to styrene monomer may be performed in the presence of a catalyst. Carbon dioxide may inhibit reaction with conventional styrene monomer process catalysts. The choice of catalyst may be any carbon dioxide/carbon monoxide tolerant ethylbenzene oxidative dehydrogenation catalyst known in the art. Preferably, the catalyst is selected from the group consisting of a vanadium and iron catalyst, a catalyst containing platinum, or a supported iron oxide catalyst.

One skilled in the art will recognize that numerous variations or changes may be made to the process described above without departing from the scope of the present invention. Accordingly, the foregoing description of preferred embodiments and following examples are intended to describe the invention in an exemplary, rather than a limiting sense.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

Example 1

By use of the present invention, the boiling point at the typical reaction system pressure of 760 mm Hg can be controlled at 122° C. by sparging into the vaporizer approximately 0.5 moles of recycle gas (carbon dioxide) for each mole of ethylbenzene. By comparison, the boiling point of pure ethylbenzene is 136° C.

Example 2

By use of the present invention, the boiling point at the typical reaction system pressure of 760 mm Hg can be controlled at 105° C. by sparging into the vaporizer approximately 1.5 moles of recycle gas (carbon dioxide) for each mole of ethylbenzene. By comparison, the boiling point of pure ethylbenzene is 136° C.

Example 3

By use of the present invention, the boiling point at the typical reaction system pressure of 760 mm Hg can be controlled at 95° C. by sparging into the vaporizer approximately 2.5 moles of recycle gas (carbon dioxide) for each mole of ethylbenzene. By comparison, the boiling point of pure ethylbenzene is 136° C.

Example 4

By use of the present invention, the boiling point at the typical reaction system pressure of 760 mm Hg can be controlled at 88° C. by sparging into the vaporizer approximately 3.5 moles of recycle gas (carbon dioxide) for each mole of ethylbenzene. By comparison, the boiling point of pure ethylbenzene is 136° C.

What is claimed is:

1. A process for the production of styrene monomer from ethylbenzene comprising the steps of:
    feeding liquid ethylbenzene feedstock into a vaporizer unit capable of converting liquid ethylbenzene to gaseous ethylbenzene, wherein the vaporizer unit produces an overhead comprising gaseous ethylbenzene;
    feeding a gaseous mixture into said vaporizer unit, wherein the gaseous mixture comprises an amount of recycle gas sufficient to lower the boiling point of ethylbenzene by at least 5° C.;
    heating the vaporizer thereby converting liquid ethylbenzene to gaseous ethylbenzene, wherein the gaseous ethylbenzene is recovered in the vaporizer overheads; and
    catalytically dehydrogenating or oxydehydrogenating the ethylbenzene in the vaporized overheads thereby catalytically producing a styrene monomer.

2. The process of claim 1 wherein the recycle gas comprises carbon dioxide.

3. The process of claim 2 wherein the recycle gas comprises approximately 90 volume % carbon dioxide.

4. The process of claim 2 wherein the gaseous mixture further comprises carbon monoxide, hydrogen, methane, argon, nitrogen and trace aromatic and aliphatic hydrocarbons.

5. The process of claim 1 wherein the gaseous mixture comprises an amount of recycle carbon dioxide sufficient to lower the boiling point of ethylbenzene below approximately 105° C. at approximately 760 mm Hg.

6. The process of claim 1 wherein the gaseous mixture comprises an amount of recycle carbon dioxide sufficient to lower the boiling point of ethylbenzene below approximately 95° C. at approximately 760 mm Hg.

7. A process for the production of styrene monomer from ethylbenzene comprising the steps of:
    feeding liquid ethylbenzene feedstock into a vaporizer unit capable of converting liquid ethylbenzene to gaseous ethylbenzene, wherein the vaporizer unit produces an overhead comprising gaseous ethylbenzene;
    feeding a gaseous mixture into said vaporizer unit, wherein the gaseous mixture comprises approximately 0.5-5 moles of recycle carbon dioxide for each mole of ethylbenzene;
    heating the vaporizer thereby converting liquid ethylbenzene to gaseous ethylbenzene, wherein the gaseous ethylbenzene is recovered in the vaporizer overheads; and
    catalytically dehydrogenating or oxydehydrogenating the ethylbenzene in the vaporized overheads thereby catalytically producing a styrene monomer.

8. The process of claim 7 wherein the gaseous mixture comprises approximately 1-2 moles of recycle carbon dioxide for each mole of ethylbenzene.

9. The process of claim 7 wherein the gaseous mixture comprises approximately 1.5 moles of recycle carbon dioxide for each mole of ethylbenzene.

10. The process of claim 7 wherein the mixture further comprises carbon monoxide, hydrogen, methane, argon, nitrogen and trace aromatic and aliphatic hydrocarbons.

* * * * *